United States Patent [19]
Baba et al.

[11] Patent Number: 5,530,138
[45] Date of Patent: Jun. 25, 1996

[54] COMPOUNDS AND USE THEREOF

[75] Inventors: Yutaka Baba; Tomoo Suzuki; Tsunemasa Suzuki; Kiyotaka Hirooka; Masayasu Kurono; Kiichi Sawai, all of Nagoya, Japan

[73] Assignee: Sanwa Kagaku Kenkyusho Co., Ltd., Aichi-ken, Japan

[21] Appl. No.: 312,638

[22] Filed: Sep. 27, 1994

[30] Foreign Application Priority Data

Oct. 6, 1993 [JP] Japan .................................. 5-250343
Aug. 17, 1994 [JP] Japan .................................. 6-193116

[51] Int. Cl.$^6$ ...................... A61K 31/40; C07D 451/02
[52] U.S. Cl. ........................................................ 548/453
[58] Field of Search ............................ 548/453; 514/413

[56] References Cited

FOREIGN PATENT DOCUMENTS

| 56-156283 | 12/1981 | Japan . |
| 61-280497 | 12/1986 | Japan . |
| 2-36183 | 2/1990 | Japan . |
| 6-184152 | 7/1994 | Japan . |

OTHER PUBLICATIONS

"Tetrahydropyridyloxadiazoles: Semirigid Muscarinic Ligands," J. Med. Chem. 1991, 34, pp. 1086–1094, Graham A. Showell et al.

"Synthesis and Muscarinic Activities of Quinuclidin-3-yltrizaole and –tetrazole Derivatives," J. Med. Chem. 1992, 35, pp. 1280–1290, Harry J. Wadsworth et al.

"Novel Functional $M_1$ Selective Muscarinic Agonists. Synthesis and Structure—Activity Relationships of 3–(1,2,5–Thiadiazolyl)–1,2,5,6–tetrahydro–1–methylpyridines," J. Med. Chem. 1992, 35, pp. 2274–2283, Per Sauerberg et al.

"Muscarinic Cholinergic Binding in Rat Brain," Proc. Nat. Acad. Sci. USA, vol. 71, No. 5, pp. 1725–1729, May 1974, Henry I. Yamamura et al.

"Multiple in Vitro Interactions with and Differential in Vivo Regulation of Muscarinic Receptor Subtypes by Tetrahydroaminoacridine," The Journal of Pharmacology and Experimental Therapeutics, vol. 250, No. 2, pp. 573–581, Donna D. Flynn et al.

*Primary Examiner*—David B. Springer
*Attorney, Agent, or Firm*—Nikaido, Marmelstein, Murray & Oram

[57] ABSTRACT

There is disclosed a compound shown by a formula of

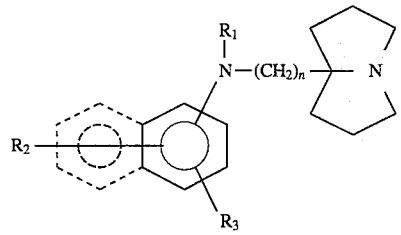

wherein $R_1$ is a hydrogen atom alkyl group having 1–4 carbon atoms or acyl group having 1–4 carbon atoms: $R_2$ and $R_3$ are a hydrogen atom, alkyl group having 1–4 carbon atoms, phenyl radical, halogen atom, cyano radical, acyl group having 1–4 carbon atoms, nitro radical, alkoxy group having 1 or 2 carbon atoms, or substituted or non-substituted amino group, respectively; n is an integer of 1–3; and dotted line means a possible ring, and a salt thereof. The compound and salt bind with muscarinic receptor in brain to develop a powerful actuation thereof and thus those can be used as an effective ingredient for preventing and curing senile dementias, and more particularly Alzheimer's disease.

4 Claims, No Drawings

COMPOUNDS AND USE THEREOF

BACKGROUND OF THE INVENTION

1. Field of the Invention

The present invention relates to novel compounds, salts thereof and use thereof as an effective ingredient for preventing and curing dementias and more particularly, a senile dementia.

2. Related Arts

In recent years, medical techniques have great advanced to prolong the average span of human life and as a result, senile dementias tend to increase. As typical senile dementias, there are a cerebral vascular dementia due to a cerebral infarction, hemorrhage or the like and an Alzheimer Type dementia, cause of which has been estimated as an atrophy or falling off of cerebral nerve cells. Symptoms of such senile dementias mainly appear as a retention defect, orientation defect or thinking disturbance, and emotional disturbance and abnormal behavior may be observed as concerned symptoms.

The Alzheimer type dementia tends to increase, as number of aged peoples of 65 years old or more increases in total population and thus it becomes one of social problems requiring urgent countermeasures including an inquiry of cause, establishment of positive remedy, various matters in a family caring for the patient. According to pathological and biochemical studies, this type dementia has possibly caused by a falling off of cerebral nerve cells, cerebral atrophy, defect on acetylcholine and other nervous conducting substances or accumulation of amyloid-$\beta$ -protein in brain. Among them, the study on acetylcholine disturbance is most advanced, but real state is under study and an excellent curing agent and therapeutics have not been found.

In recent years, THA (1,2,8,4-tetrahydro-9-aminoacridine) was developed in USA, as an agent for curing the Alzheimer type dementia, to give a topic with great interests. However, recent news report that an effectiveness and a certain side effect of THA were called in question.

Therefore, it was anxious to develop such an agent for preventing and curing dementias that its pharmacological effects ensurely appear and has low toxicity.

Starting from the development of said THA, developments on anti-dementia agents have been proceeded in various countries in the world and main current thereof lies in developing an agent for activating acetylcholinic nervous conducting substances. There are 3 strategies for activating acetylcholinic nervous conducting functions.

Namely, the first measure is an exhibition of acetylcholine esterass to increase a concentration of acetylcholine decreased in brain, second is an acceleration of acetylcholine discharge in synapse, and third is a binding with an acetylcholine receptor to actuate the receptor.

Said THA shows an inhibition to acetylchotine esterass but its action cannot be said as powerful. At the present time, the main current in the development lies in providing a substance for actuating muscarinic acetylcholine receptors, based on the third strategy, which has been studied by various laboratories. There are 2 muscarinic acetylcholine receptors in brain, namely muscarine 1 receptor and muscarine 2 receptor and it has been reported that actuation of muscarine 1 shows higher activity than that of muscarine 2 ["J. Med. Chem.", Vol. 34, page 1086 (1991); "J. Med. Chem.", Vol. 35, page 1280 (1992); "J. Med. Chem.", Vol. 35, page 2274 (1992), Jap. Pat. No. Sho 61 (A.D. 1986) - 280497(A) and Jap. Pat. No. Hei 2 (A.D. 1990) - 36183(A)].

The compounds according to the present invention, as shown later, has 1-azabicyclo[3.3.0]octane ring. In Jap. Pat. No. Hei 3 (A.D. 1991) - 38272, there are disclosed compounds with such a ring and analogous skeleton, including following compound, but the official gazette doe not refer to an actuation activity of muscarinic acetylcholine receptor.

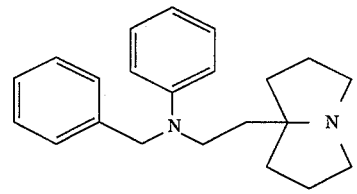

SUMMARY OF THE INVENTION

An object of the invention is to provide an anti-dementia compound having a powerful activity To actuate muscarine 1 receptor and high safety in use.

The inventors have studied and investigated for developing anti-dementia compounds, also in the past, to file patent applications in Japan [Jap. Pat. Appln. Nos. Hei 3 (A.D. 1991) - 302070 and Hei 4 (A.D. 1992) - 283848 (claiming a domestic priority of the former application) which was opened on Jul. 5, 1994 as Jap. Pat. No. Hei 6 (A.D. 1994) - 184182(A)].

In the official gazette of Jap. Pat. No. Hei 8 (A.D. 1994) - 184152(A), there are disclosed following compounds and salts thereof.

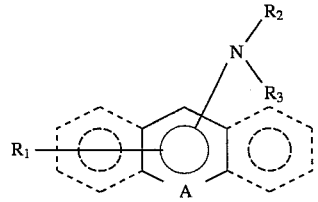

wherein A is CH, N or N→O; $R_1$ is nitro or amino radical; $R_2$ is a hydrogen atom, lower alkyl or acyl group; $R_3$ is a radical of

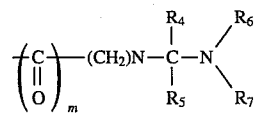

in which m is an integer of 0 or 1; n is an integer of 1–3; $R_4$ and $R_5$ are a hydrogen atom or lower alkyl group, respectively: $R_6$ and $R_7$ are a hydrogen atom, or straight- or branched-chain lower alkyl group, respectively; and $R_4$ and $R_6$ or $R_5$ and $R_7$ may form a heterocyclic ring with an alkylene chain, and dotted line means a possible ring.

The inventors further studied and investigated for developing compounds with said desired properties to confirm that various compounds belonging to those defined by said general formula and shown by following general formula show the receptor actuation activity same with or higher than those concretely disclosed in the official gazette to establish the invention.

According to the invention, such a compounds and non-toxicic salts thereof are provided that it has a skeleton or basic structure shown by a formula (I) of

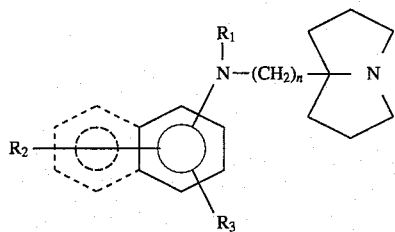

wherein $R_1$ is a hydrogen atom, alkyl group having 1–4 carbon atoms or acyl group having 1–4 carbon atoms; $R_2$ and $R_3$ are a hydrogen atom, alkyl group having 1–4 carbon atoms, phenyl radical, halogen atom, cyano radical, acyl group having 1–4 carbon atoms, nitro radical, alkoxy group having 1 or 2 carbon atoms, or substituted or non-substituted amino group, respectively; n is an integer of 1–3; and dotted line means a possible ring, and selected from the group consisting of (1) 1-[N-(1-azabicyclo[3.3.0]octan-5-yl)methyl-N-methylamino]-4-chloronaphthalene,
(2) 1-[N-(1-azabicyclo[3.3.0]octan-5-yl)methyl-N-formylamino]-4-methoxynaphthalene,
(3) 1-[N-(1-azabicyclo[3.3.0]octan-5-yl)methyl-N-methylamino]-4-methoxynaphthalene,
(4) 1-(1-azabicyclo[3.3.0]octan-5-yl)methylamino-4-methoxynaphthalene,
(5) 1-[N-(1-azabicyclo[3.3.0]octan-5-yl)methyl-N-formylamino]naphthalene,
(6) 1-(1-azabicyclo[3.3.0]octan-5-yl)methyl-N-methylamino]-naphthalene,
(7) 1-[N-(1-azabicyclo[3.3.0]octan-5-yl)methyl-N-formylamino]-4-fluoronaphthalene,
(8) (1-azabicyclo[3.3.0]octan-5-yl)methyl-N-methylamino]-4-fluoronaphthalene,
(9) 1-{N-[2-(1-azabicyclo[3.3.0]octan-5-yl)ethyl]-N-formylamino}naphthalene,
(10) 1-{N-[2-(1-azabicyclo[3.3.0]octan-5-yl)ethyl]-N-methylamino}naphthalene,
(11) 1-[2-(1-azabicyclo[3.3.0]octan-5-yl)ethyl]aminonaphthalene,
(12) 1-[N-(1-azabicyclo[3.3.0]octan-5-yl)methyl-N-ethylamino]-4-nitronaphthalene,
(13) N-(1-azabicyclo[3.3.0]octan-5-yl)methyl-N-formylaniline,
(14) N-(1-azabicyclo[3.3.0]octan-5-yl)methyl-N-methylaniline,
(15) N-[2-(1-azabicyclo[3.3.0]octan-5-yl)ethyl]-N-formylaniline,
(16) N-[2-(1-azabicyclo[3.3.0]octan-5-yl)ethyl]-N-methylaniline,
(17) N-(1-azabicyclo[3.3.0]octan-5-yl)methyl-N-methyl-2-nitroaniline,
(18) N-(1-azabicyclo[3.3.0]octan-5-yl)methyl-N-methyl-4-nitroaniline,
(19) N-(1-azabicyclo[3.3.0]octan-5-yl)methyl-N-formyl-2-phenylaniline,
(20) N-(1-azabicyclo[3.3.0]octan-5-yl)methyl-N-methyl-2-phenylaniline,
(21) N-(1-azabicyclo[3.3.0]octan-5-yl)methyl-N-formyl-3-phenylaniline,
(22) N-(1-azabicyclo[3.3.0]octan-5-yl)methyl-N-methyl-3-phenylaniline,
(23) N-[2-(1-azabicyclo[3.3.0]octan-5-yl)ethyl]-2-nitroaniline,
(24) N-[2-(1-azabicyclo[3.3.0]octan-5-yl)ethyl]-4-nitroaniline,
(25) N-[2-(1-azabicyclo[3.3.0]octan-5-yl)ethyl]-N-methyl-2-nitroaniline,
(26) N-[2-(1-azabicyclo[3.3.0]octan-5-yl)ethyl]-N-methyl-4-nitroaniline,
(27) 2-[2-(1-azabicyclo[3.3.0]octan-5-yl)ethylamino]benzonitrile,
(28) 4-[2-(1-azabicyclo[3.3.0]octan-5-yl)ethylamino]benzonitrile,
(29) 2-{[2-(1-azabicyclo[3.3.0]octan-5-yl)ethyl]methylamino}benzonitrile,
(30) N-[2-(1-azabicyclo[3.3.0]octan-5-yl)ethyl]-2-chloroaniline,
(31) N-[2-(1-azabicyclo[3.3.0]octan-5-yl)ethyl]-2-fluoroaniline,
(32) N-[2-(1-azabicyclo[3.3.0]octan-5-yl)ethyl]-4-fluoro-2-nitroaniline,
(33) 2-{[2-(1-azabicyclo[3.3.0]octan-5-yl)ethyl]amino}benzamide, and
(34) 2-[(1-azabicyclo[3.3.0]octan-5-yl)methylamino]benzonitrile.

Namely, these compounds and sales thereof show an excellent anti-dementia activity.

As acids for forming the non-toxicic salts, following acids can be listed: hydrochloric acid, sulfuric acid, hydrobromic acid, hydroiodic acid, phosphoric acid or The like inorganic acid; fumaric acid, maleic acid, tartaric acid, citric acid, methanesulfonic acid, acetic acid, succinic acid, lactic acid or the like organic acid; and aspattic acid, glutamic acid or the like amino acid.

The compounds and salts thereof according to the invention can be prepared one of following routes.

Route 1

In this route, a compound shown in the following formula (II) is converted into a diazo-compound, and then halogenated and cyanated, and if necessary, converted into a salt.

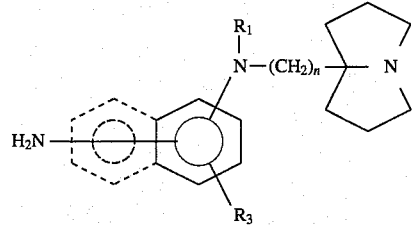

wherein $R_1$ is a hydrogen atom, alkyl group having 1–4 carbon atoms or acyl group having 1–4 carbon atoms; $R_3$ is a hydrogen atom, phenyl radical, halogen atom, cyano radical, acyl group having 1–4 carbon atoms, nitro radical or alkoxy group having 1 or 2 carbon atoms; n is an integer of 1–3; and dotted line means a possible ring.

In case of converting into the diazo-compound, water, acetic acid, tetrahydrofuran, dimethylsulfoxide, pyridine or the like is used as the solvent; hydrochloric acid, sulfuric acid, hydrobromic acid, borofluoric acid (in case of fluoration, only) or the like is added as the acid; and sodium nitrite is added in a molar ratio of 0.8–1.1 to the raw material (II). The reaction is carried out at a temperature of $-10°-+20°$ C.

For obtaining fluorated compound, a solid diazo-compound to be crystallized as tetrafluoroboronate is filtered and then subjected to decomposition under influence of heat or light-beam. For accelerating the decomposition, cuprous chloride, sodium hydroxide or the like may be added.

Chrolinated compound can be obtained by reacting the diazo-compound in a state of solution or suspension with cuprous chloride in hydrochloric acid or metallic copper in hydrochloric acid.

Brominated compound can be obtained by reacting the diazo-compound in a state of solution or suspension with bromine, cuprous bromide or sodium bromide in hydrobromic acid solution. In this case, metallic copper may be added. The brominated compound can also be obtained by adding the diazo-compound into cuptic bromide solution containing mercuric bromide to obtain separating solids, and adding potassium bromide or dimethylaniline to cause thermal decomposition thereof.

Iodinated compound can be obtained by reacting the diazo-compound compound in a state of solution or suspension with potassium iodide or hydroiodic acid.

Cyanated compound can be obtained by reacting the diazo-compound in a state of solution. (aqueous solution or acetic acid solution), suspension or solid with cuprous cyanide, sodium cyanide, potassium cyanide, nickel cyanide or a mixture thereof.

A separation and purification of the objective compound from the reaction mixture can be carried out through operations known per se, for instance, filtration, concentration, extraction, column chromatography, distillation, recrystallization and the like.

Route 2

In this route, a compound having a formula (III) of

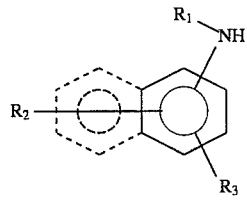

wherein $R_1$ is a hydrogen atom, alkyl group having 1–4 carbon atoms, acyl group having 1–4 carbon atoms; $R_2$ and $R_3$ are hydrogen atom, phenyl radical, halogen atom, cyano radical, acyl group having 1–4 carbon atoms, nitro radical or alkoxy group having 1 or 2 carbon atoms, respectively; and dotted line means a possible ring, is reacted with a compound having a formula (IV) of

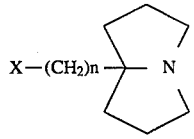

wherein X is a halogen atom; and n is an integer of 0–3, and if necessary, the resulting compound is converted into a salt.

In this route, the molar ratio of the raw materials (III) and (IV) is about 1:0.8–1:3.0. The reaction can be carried out in the presence or absence of a solvent and at a temperature of −60°–+180° C. As the solvent, followings can be listed: benzene, toluene, xylene or the like aromatic hydrocarbon; nitrobenzene, chlorobenzene, dichlorobenzene or the like substituted aromatic hydrocarbon; N,N-dimethylformamide, N,N-dimethylacetamide, dimethylsulfoxide or the like aprotic polar solvent; methylene chloride, chloroform or the like chlorinic solvent; pyridine, triethylamine or the like basic solvent; and diethylether, tetrahydrofuran or the like ether. If necessary, such a base may be added as sodium hydroxide, sodium carbonate, potassium carbonate, sodium hydride, sodium amide or the like.

Procedures for separating and purifying the objective compound from the reaction mixture are same with those for Route 1.

Route 3

In this route, a compound shown in the following formula (V) is subjected to reduction or deacylation and if necessary, the resulting compound is converted into a salt.

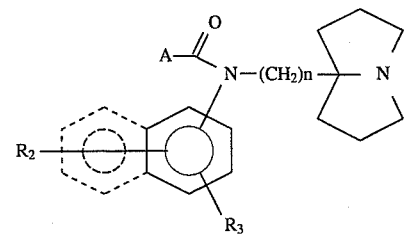

wherein $R_1$ is a hydrogen atom, alkyl group having 1–4 carbon atoms or acyl group having 1–4 carbon atoms; $R_2$ and $R_3$ are a hydrogen atom, alkyl group having 1–4 carbon atoms, phenyl radical, halogen atom, cyano radical, acyl group having 1–4 carbon atoms, nitro radical or alkoxy group having 1 or 2 carbon atoms, respectively; and dotted line means a possible ring.

In this method, the compound shown by formula (V) is reacted with a metal hydride reduction reagent such as lithium aluminum hydride, aluminum hydride, diisobuthylaluminum hydride, borane or the like. As a solvent, diethylether, diisopropylether, dimethoxyethane, tetrahydrofuran or the like can be used and the reaction is carried out at a temperature of −50°–+100° C.

Procedures are same with those for Route 1.

Route 4

In this route, a compound shown by a formula (VI) of

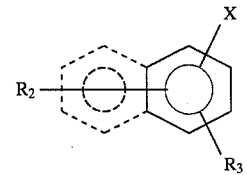

wherein X is a halogen atom or alkoxy group having 1 or 2 carbon atoms; $R_2$ and $R_3$ are a hydrogen atom, alkyl group having 1–4 carbon atoms, phenyl radical, halogen atom, cyano radical, acyl group having 1–4 carbon atoms or nitro radical, respectively; n is an integer of 1–3; and dotted line means a possible ring, is reacted with a compound shown by a formula (VII) of

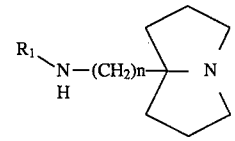

wherein $R_1$ is a hydrogen atom or alkyl group having carbon atoms; and n is an integer of 1–3, and if necessary, the resulting compound is converted into a salt.

In this route, the molar ratio of the raw materials (VI) and (VII) is about 1:0.8–1:5.0. The reaction can be carried out in the presence or absence of a solvent and at a temperature of 0°–180° C. As the solvents, followings can be listed: methanol, ethanol, isopropanol or the like alcohol; benzene, toluene, xylene or the like aromatic hydrocarbon; N,N-dimethylformamide, N,N-dimethylacetamide, dimethylsulfoxide or the like aprotic polar solvent; methylene chloride, chloroform or the like chlorinic solvent; pyridine, triethylamine or the like basic solvent; and diethylether, tetrahydrofuran or the like ether. If necessary, a catalyst such as sodium iodide, sodium bromide or the like may be added.

Procedures are same with those for Route 1.

The compounds and salts thereof can be made into a medicine by composing at least one of them as an effective ingredient. There is no limitation in dosage form for preparing the medicine and thus, a solid medicine such as tablet, pill, hard capsule, soft capsule, powder, fine subtila, granule or suppository, or a liquid medicine such as solution, suspension or emulsion can be obtained in a conventional manner.

A dose of the compound or salt thereof changes by various factors such as a kind of the compound or salt, degree of disease, age and symptom of the patient and others, but for adult, it is preferable to give 0.001–1000 mg/day and more preferably, 0.01–100 mg/day.

DETAILED DESCRIPTION OF THE PREFERRED EMBODIMENT

The invention will now be further explained with reference to Examples for preparing compounds and salts as well as Pharmacological Example.

EXAMPLE 1

1-[N-(1-Azabicyclo[3.3.0]octan-5-yl)methyl-N-methylamino]-4-chloronaphthalene

To 6.31 g (21.4 mmol) of N-(1-azabicyclo[3.3.0]octan-5-yl)methyl-N-methyl-1,4-diaminonaphthalene, water (27.5 ml) and concentrated sulfuric acid (55 ml) were added to dissolve the compound therein. Sodium nitrite (1.40 g, 20.3 mmol) in water (8 ml) was added dropwise to the solution at a temperature of −5+ C. and then stirred for 15 minutes. Cuprous chloride (8.50 g, 85.9 mmol) suspended in concentric hydrochloric acid (18 ml) was added dropwise into the solution which was kept at 85° C. under stirring condition. After further stirring for 5 minutes, the reaction mixture was cooled by water with ice pieces. Several ice pieces were added to the reaction mixture which was made alkaline by adding 10% aqueous sodium hydroxide solution and extracted by chloroform. The resulting organic layer was dried over anhydrous sodium sulfate, concentrated in vacuo, purified by column chromatography to afford the desired compound (950 mg, 14.1% ), as a colorless liquid.

MS spectrum (EI/DI) m/z: 314 (M⁻), 110 (base peak).

IR spectrum (neat) cm$^{-1}$: 2950, 1460, 760.

$^1$H-NMR spectrum (CDCl$_3$) δppm:

| 1.5–2.0 | (8H, m), |
| --- | --- |
| 2.5–2.6 | (2H, m), |
| 2.89 | (3H, s), |
| 3.0–3.1 | (2H, m), |
| 3.16 | (2H, s), |
| 7.16 | (1H, d, J=8Hz), |
| 7.48 | (1H, d, J=8Hz), |
| 7.5–7.6 | (2H, m), |
| 8.2–8.4 | (2H, m). |

EXAMPLE 2

(1-Azabicyclo[3.3.0]octan-5-yl)methyl-N-formylamino]-4-methoxynaphthalene

To ice-chilled N-formyl-4-methoxy-1-naphtylamine (5.50 g, 22.4 mmol) in DMF (40 ml), 60% sodium hydride (dispersed in oil, 4.48 g, 112 mmol) was added and stirred. 5-chloromethyl-1-azabicyclo[3.3.0]octane (hydrochloride, 5.26 g, 26.8 mmol) in DMF (20ml) was added dropwise To the solution at −15° C. and the mixture was stirred at 25° C. for 1.5 hours. The reaction mixture was poured on ice, extracted by chloroform, dried over anhydrous sodium sulfate, concentrated in vacuo, and purified by chromatography to afford the desired compound (6.60 g, 91.0%), as a colorless liquid.

MS spectrum [CI/DI (i-Bu)] m/z: 325 (M+1)⁻, 110 (base peak).

IR spectrum (neat) cm$^{-1}$: 3500, 2950, 1680.

$^1$H-NMR spectrum (CDCl$_3$) δppm:

| 1.2–1.8 | (8H, m), |
| --- | --- |
| 2.4–2.6 | (2H, m), |
| 2.9–3.1 | (2H, m), |
| 3.6–4.1 | (1H, m), |
| 4.04 | (3H, s), |
| 6.80 | (1H, d, J=8Hz), |
| 7.31 | (1H, d, J=8Hz), |
| 7.5–7.7 | (2H, m), |
| 7.76 | (1H, dd, J=7, 2Hz), |
| 8.27 | (1H, s), |
| 8.33 | (1H, dd, J=7, 2Hz). |

EXAMPLE 3

1-[N-(1-Azabicyclo[3.3.0]octan-5-yl)methyl-N-methylamino]-4-methoxynaphthalene

To 1M borane-THF complex solution (40.0 ml, 40.0 mmol), 1-[N-(1-azabicyclo[3.3.0]octan-5-yl)methyl-N-formylamino]-4-methoxynaphthalene (2.90 g, 8.95 mmol) in absolute THF (20 ml) was added dropwise at 25° C. After refluxed for 1 hour, the reaction mixture was cooled, refluxed for 10 minutes subsequent to addition of 6N-HCl (10 ml), concentrated in vacuo, made into alkaline by addition of sodium hydroxide pellets, extracted by ethyl ether, dried over anhydrous sodium sulfate, concentrated in vacuo, and purified by chromatography to afford the desired compound (2.66 g, 96.0%), as a colorless liquid.

MS spectrum [CI/DI (i-Bu)] m/z: 311 (M+1)⁻, 110 (base peak).

IR spectrum (neat) cm$^{-1}$: 2980, 1580, 1220.

$^1$H-NMR spectrum (CDCl$_3$) δppm:

| 1.4–1.5 | (2H, m), |
| --- | --- |
| 1.6–1.8 | (4H, m), |
| 1.9–2.0 | (2H, m), |
| 2.5–2.6 | (2H, m), |
| 2.82 | (3H, s), |
| 3.0–3.1 | (2H, m), |
| 3.11 | (2H, s), |
| 3.97 | (3H, s) |
| 6.75 | (1H, d, J=8Hz), |
| 7.19 | (1H, d, J=8Hz), |
| 7.4–7.5 | (2H, m), |
| 8.23 | (1H, dd, J=7, 2Hz), |
| 8.34 | (1H, dd, J=7, 2Hz). |

EXAMPLE 4

1-(1-Azabicyclo[3.3.0]octan-5-yl)-
methylamino-4-methoxynaphthalene

To lithium aluminum hydride (1.76 g, 46.3 mmol) in THF (43 ml), 1-[N-(1-Azabicyclo[3.3.0] octan-5-yl )methyl-N-formylamino]-4 -methoxynaphthalene (3.00 g, 9.26 mmol) in THF (15 ml) was added dropwise at room temperature. After refluxed for 1 hour, the reaction mixture was cooled and chilled water was added dropwise. Formed solids were removed by filtration and the filtrate was concentrated in vacuo and purified by chromatography to afford the desired compound (1.80 g, 62.7%), as a pale yellow liquid.

MS spectrum [CI/DI (i-Bu)] m/z: 297 (M+1)$^-$, 110 (base peak).

IR spectrum (neat) cm$^{-1}$: 2950, 1590, 1220.

$^1$H-NMR spectrum (CDCl$_3$) δppm:

| | |
|---|---|
| 1.6–2.0 | (8H, m), |
| 2.7–2.8 | (2H, m), |
| 3.03 | (2H, s), |
| 3.1–3.2 | (2H, m), |
| 3.94 | (3H, s), |
| 6.50 | (1H, d, J=8Hz), |
| 6.73 | (1H, d, J=8Hz), |
| 7.4–7.5 | (2H, m), |
| 7.8–7.9 | (1H, m), |
| 8.2–8.3 | (1H, m). |

EXAMPLE 5

1-[N-(1-Azabicyclo[3.3.0]octan-5-yl)methyl-N-formylamino]-naphthalene

The procedures described in Example 2 were repeated except that N-formyl-1-naphthylamine (1.83 g, 10.7 mmol) and 5-chloromethyl-1-azabicyclo[3.3.0]octane (hydrochloride, 2.30 g, 11.7 mmol) were employed. In this case, the desired compound was obtained as a colorless liquid (3.02 g, 95.9%

MS spectrum (EI/DI) m/z : 294 (M$^-$) 110 (base peak).

IR spectrum (neat) cm$^{-1}$: 3600, 2950, 1680.

$^1$H-NMR spectrum (CDCl$_3$) δppm:

| | |
|---|---|
| 1.2–1.8 | (8H, m), |
| 2.4–2.6 | (2H, m), |
| 2.9–3.1 | (2H, m), |
| 3.25 | (1H, d, J=13Hz), |
| 4.10 | (1H, d, J=13Hz), |
| 7.4–7.6 | (4H, m), |
| 7.8–8.0 | (3H, m), |
| 8.31 | (1H, s). |

EXAMPLE 6

1-[N-(1-Azabicyclo[3.3.0]octan-5-yl)methyl-N-methylamino]-naphthalene

The procedures described in Example 3 were repeated except that 1-[N-(1-azabicyclo[3.3.0]octan-5 -yl)methyl-N-formylamino]naphthalene (2.89 g, 9.82 mmol) was employed. In this case, the desired compound was obtained as a pale yellow liquid (2 49 g, 90.4%).

MS spectrum (EI/DI) m/z: 280 (M$^-$) 170, 110 (base peak).

IR spectrum (neat) cm$^{-1}$: 2950, 1580, 1400, 780.

$^1$H-NMR spectrum (CDCl$_3$) δppm:

| | |
|---|---|
| 1.5–1.6 | (2H, m), |
| 1.7–1.8 | (4H, m), |
| 2.0–2.1 | (2H, m), |
| 2.5–2.6 | (2H, m), |
| 2.90 | (3H, s), |
| 3.0–3.1 | (2H, m), |
| 3.18 | (1H, s), |
| 7.25 | (1H, d, J=7Hz), |
| 7.4–7.5 | (3H, m), |
| 7.54 | (1H, d, J=8Hz), |
| 7.8–7.9 | (1H, m), |
| 8.3–8.4 | (1H, m). |

EXAMPLE 7

1-[N-(1-Azabicyclo[3.3.0]octan-5-yl)methyl-N-formylamino]-4-fluoronaphthalene

The procedures described in Example 2 were repeated except that 4-fluoro-N-formyl-1-naphthylamine (1.90 g, 10.0 mmol) and 5 -chloromethyl-1-azabicyclo[3.3.0]octane (hydrochloride, 2.17 g, 11.1 mmol) were employed. In this case, the desired compound was obtained as a pale yellow liquid (2.90 g, 92.8%).

MS spectrum (EI/DI) m/z: 312 (M$^-$) 283, 110 (base peak).

IR spectrum (neat) cm$^{-1}$: 3500, 2950, 1680.

$^1$H-NMR spectrum (CDCl$_3$) δppm:

| | |
|---|---|
| 1.3–1.8 | (8H, m), |
| 2.5–2.6 | (2H, m), |
| 2.9–3.0 | (2H, m), |
| 3.65 | (1H, d, J=14Hz), |
| 4.11 | (1H, d, J=14Hz), |
| 7.20 | (1H, dd, J=10, 8Hz), |
| 7.36 | (1H, dd, J=8, 5Hz), |
| 7.6–7.7 | (2H, m), |
| 7.8–7.9 | (1H, m), |
| 8.1–8.9 | (1H, m). |

EXAMPLE 8

1-[N-(1-Azabicyclo[3.3.0]octan-5-yl)methyl-N-methylamino]-4-fluoronaphthalene

The procedures described in Example 3 were repeated except that 1-[N-(1-azabicyclo[3.3.0]octan-5-yl)methyl-N-formylamino]-4-fluoronaphthalene (2.78 g, 8.90 mmol) was employed. In this case, the desired compound was obtained as a pale yellow liquid (2.55 g, 96.0%).

MS spectrum (EI/DI) m/z: 298 (M$^-$) 284, 110 (base peak).

IR spectrum (neat) cm$^{-1}$: 2950, 1465, 1390, 1050.

$^1$H-NMR spectrum (CDCl$_3$) δppm:

| | |
|---|---|
| 1.4–1.5 | (2H, m), |
| 1.6–1.8 | (4H, m), |
| 1.9–2.0 | (2H, m), |
| 2.0–2.6 | (2H, m), |
| 2.83 | (3H, s), |
| 3.0–3.1 | (2H, m), |
| 3.12 | (2H, s), |
| 7.05 | (1H, dd, J=10, 8Hz), |
| 7.17 | (1H, dd, J=8, 8Hz), |
| 7.5–7.6 | (2H, m), |
| 8.0–8.1 | (2H, m), |
| 8.3–8.4 | (2H, m). |

EXAMPLE 9

1-{N-[2-(1-Azabicyclo[3.3.0]octan-5-yl)ethyl]-N-formylamino}naphthalene

The procedures described in Example 2 were repeated except that N-formyl-1-naphthylamine (1.90 g, 11.1 mmol) and 5-(2-chloroethyl)-1-azabicyclo[3.3.0]octane (hydrochloride, 2.57 g, 12.2 mmol) were employed In this case, the desired compound was obtained as a colorless liquid (1.80 g, 52.6%)

MS spectrum (EI/DI)m/z: 308 (M$^-$) 280, 110 (base peak).
IR spectrum (neat) cm$^{-1}$: 3600, 2950, 1680.
$^1$H-NMR spectrum (CDCl$_3$) δppm:

| | |
|---|---|
| 1.5–1.9 | (12H, m), |
| 2.5–2.6 | (2H, m), |
| 2.9–3.0 | (2H, m), |
| 7.33 | (1H, dd, J=10, 7Hz), |
| 7.5–7.6 | (3H, m), |
| 7.8–7.9 | (3H, m), |
| 8.21 | (1H, s). |

EXAMPLE 10

1-{N-[2-(1-Azabicyclo[3.3.0]octan-5-yl)ethyl]-N-methylamino} naphthalene

The procedures described in Example 3 were repeated except that 1-{N-[2-(1-azabicyclo[3.3.0] octan-5-yl)ethyl]-N-formylamino}naphthalene (1.70 g, 5.51 mmol) was employed. In this case, the desired compound was obtained as a colorless liquid (1.51. g, 93.1%).

MS spectrum (EI/DI) m/z: 294 (M$^-$) 279, 110 (base peak).
IR spectrum (neat) cm$^{-1}$: 2950, 1580, 1400, 770.
$^1$H-NMR spectrum (CDCl$_3$) δppm:

| | |
|---|---|
| 1.4–1.5 | (2H, m), |
| 1.7–1.8 | (8H, m), |
| 2.5–2.6 | (2H, m), |
| 2.86 | (3H, s), |
| 2.9–3.0 | (2H, m), |
| 3.1–3.2 | (2H, s), |
| 7.10 | (1H, d, J=12, 9Hz), |
| 7.4–7.5 | (3H, m), |
| 7.51 | (1H, d, J=8Hz), |
| 7.8–7.9 | (1H, m), |
| 8.2–8.3 | (1H, m). |

EXAMPLE 11

1-[2-(1-Azabicyclo[3.3.0]octan-5-yl)ethyl] aminonaphthalene

The procedures described in Example 4 were repeated except that 1-{N-[2-(1-azabicyclo[3.3.0] octan-5-yl)ethyl]-N-formylamino}naphthalene (1.60 g, 5.18 mmol) was employed. In this case, the desired compound was obtained as a pale yellow liquid (1.05 g, 72.4%).

MS spectrum (EI/DI) m/z: 280 (M$^-$) 110 (base peak).
IR spectrum (neat) cm$^{-1}$: 8200, 2950, 1580, 1410.
$^1$H-NMR spectrum (CDCl$_3$) δ ppm:

| | |
|---|---|
| 1.6–1.9 | (8H, m), |
| 1.94 | (2H, t, J=6Hz), |
| 2.6–2.7 | (2H, m), |
| 3.1–3.2 | (2H, m), |
| 3.35 | (2H, t, J=6Hz), |
| 6.48 | (1H, d, J=7Hz), |
| 7.14 | (1H, d, J=8Hz), |
| 7.33 | (1H, t, J=8Hz), |
| 7.4–7.3 | (2H, m), |
| 7.7–7.8 | (1H, m), |
| 7.8–7.9 | (1H, m), |

EXAMPLE 12

1-[N-(1-Azabicyclo[3.3.0]octan-5-yl)-methyl-N-ethylamino]-4-nitronaphthalene

1-Chloro-4-nitronaphthalene (2.00 g, 9.63 mmol), 5-ethylaminomethyl-1-azabicyclo[3.3.0]octane (3.24 g, 19.3 mmol) and sodium iodide (580 mg) were added into anhydrous pyridine (20.0 ml) to react the mixture in a sealed tube for 20 hours at 190° C. After addition of aqueous sodium hydroxide solution subsequent to concentration in vacuo, the reaction mixture was extracted by ethyl acetate, dried over anhydrous sodium sulfate, concentrated in vacuo, and purified by column chromatography to afford the desired compound (1.00 g, 30.6%), as a yellow liquid.

MS spectrum (EI/DI) m/z: 339 (M$^-$) 310, 110 (base peak).
IR spectrum (neat) cm$^{-1}$: 2950, 1570, 1310, 770.
$^1$H-NMR spectrum (CDCl$_3$) δppm:

| | |
|---|---|
| 0.99 | (3H, t, J=7Hz), |
| 1.4–1.5 | (2H, m), |
| 1.7–1.9 | (6H, m), |
| 2.5–2.6 | (2H, m), |
| 2.9–3.0 | (2H, m), |
| 3.33 | (2H, m), |
| 3.44 | (2H, q, J=7Hz), |
| 7.26 | (1H, d, J=8Hz), |
| 7.5–7.7 | (2H, m), |
| 8.3–8.4 | (2H, m), |
| 8.74 | (1H, d, J=8Hz). |

EXAMPLE 13

1-(Azabicyclo[3.3.0]octan-5-yl)methyl-N-methyl-N-formylaniline,

The procedures described in Example 2 were repeated except that formanilide (1.90 g, 15.7 mmol) and 5-chloromethyl-1-azabicyclo[8.3.0] octane(hydrochloride, 3.38 g, 17.2 mmol) were employed. In this case, the desired compound was obtained as a pale yellow liquid (8.65 g, 95.1%).

MS spectrum [CI/DI (i-Bu)] m/z: 245 (M+1)$^-$ (base peak), 110.
IR spectrum (neat) cm$^{-1}$: 3500, 2960, 1680, 1600, 1360.
$^1$H-NMR spectrum (CDCl$_3$) δppm:

| | |
|---|---|
| 1.2–1.3 | (2H, m), |
| 1.6–1.8 | (6H, m), |
| 2.5–2.6 | (2H, m), |
| 2.9–3.0 | (2H, m), |
| 3.83 | (2H, s), |
| 7.2–7.5 | (5H, m), |
| 8.35 | (1H, s). |

EXAMPLE 14

N-(1-Azabicyclo[3.3.0]octan-5-yl)methyl]-N-methylaniline

The procedures described in Example 3 were repeated except that N-(1-azabicyclo[3.3.0]octan-5-yl)methyl-N-formylaniline (2.80 g, 11.5 mmol) was employed. In this case, the desired compound was obtained as a colorless liquid (2.45 g, 92.5%).

MS spectrum (EI/DI) m/z: 230 (M⁻) 110 (base peak).

IR spectrum (neat) cm$^{-1}$: 2960, 1600, 1510, 750.

$^1$H-NMR spectrum (CDCl$_3$) δppm:

| | |
|---|---|
| 1.5–1.6 | (2H, m), |
| 1.6–1.9 | (6H, m), |
| 2.5–2.6 | (2H, m), |
| 3.0–3.1 | (2H, m), |
| 3.04 | (3H, s), |
| 3.27 | (2H, s), |
| 6.65 | (1H, t, J=7Hz), |
| 6.7–6.8 | (2H, m), |
| 7.2–7.3 | (2H, m). |

EXAMPLE 15

N-[2-(1-Azabicyclo[3.3.0]octan-5-yl)ethyl-N-formylaniline

The procedures described in Example 2 were repeated except that formanilide (1.80 g, 14.9 mmol) and 5-(2-chloroethyl)-1-azabicyclo[3.3.0]octane (hydrochloride, 3.43 g, 16.3 mmol) were employed. In this case, the desired compound was obtained as a pale yellow liquid (3.39 g, 88.1%).

MS spectrum (EI/DI) m/z: 258 (M⁻) 230, 110 (base peak).

IR spectrum (neat) cm$^{-1}$ : 3500, 2950, 1680, 1600.

$^1$H-NMR spectrum (CDCl$_3$) δppm:

| | |
|---|---|
| 1.5–1.8 | (10H, m), |
| 2.5–2.6 | (2H, m), |
| 2.9–3.0 | (2H, m), |
| 3.8–3.9 | (2H, s), |
| 7.2–7.4 | (5H, m), |
| 8.38 | (1H, s). |

EXAMPLE 16

N-[2-(1-Azabicyclo[3.3.0]octan-5-yl)ethyl]-N-methylaniline

The procedures described in Example 3 were repeated except that N-[2-(1-azabicyclo[3.3.0]octan-5-yl)ethyl-N-formylaniline (2.60 g, 10.1 mmol) was employed. In this case, the desired compound was obtained as a colorless liquid (2.01 g, 81.4%).

MS spectrum (EI/DI) m/z: 244 (M⁻), 120, 110 (base peak).

IR spectrum (neat) cm$^{-1}$: 2950, 1600, 1510, 750.

$^1$H-NMR spectrum (CDCl$_3$) δppm:

| | |
|---|---|
| 1.5–1.8 | (10H, m), |
| 2.5–2.6 | (2H, m), |
| 2.90 | (3H, s), |
| 2.9–3.0 | (2H, m), |
| 3.3–3.4 | (2H, m), |
| 6.6–6.7 | (3H, m), |
| 7.2–7.3 | (2H, m). |

EXAMPLE 17

N-(1-Azabicyclo[3.3.0]octan-5-yl]methyl-N-methyl-2-nitroaniline

The procedures described in Example 12 were repeated except that 1-chloro-2-nitrobenzene (1.27 g, 8.06 mmol) and methylaminomethyl-1-azabicyclo[3.3.0]octane (2.50 g, 16.2 mmol) were employed. In this case, the desired compound was obtained as a yellow liquid (1.20 g, 54.1%).

MS spectrum [CI/DI (i-Bu)] m/z: 276 (M+1)⁻, 110 (base peak).

IR spectrum (neat) cm$^{-1}$: 2950, 1600, 1340, 740.

$^1$H-NMR spectrum (CDCl$_3$) δ ppm:

| | |
|---|---|
| 1.5–1.6 | (2H, m), |
| 1.6–1.9 | (6H, m), |
| 2.5–2.6 | (2H, m), |
| 2.90 | (3H, s), |
| 2.9–3.0 | (2H, m), |
| 3.26 | (2H, s), |
| 6.8–6.9 | (1H, m), |
| 7.2–7.4 | (2H, m), |
| 7.7–7.8 | (1H, m). |

EXAMPLE 18

N-(1-Azabicyclo[3.3.0]octan-5-yl]methyl-N-methyl-4-nitroaniline

The procedures described in Example 12 were repeated except that 1-chloro-4-nitrobenzene (1.27 g, 8.06 mmol) and methylaminomethyl-1-azabicyclo[3.3.0]octane (2.50 g, 16.2 mmol) were employed. In this case, the desired compound was obtained as a yellow liquid (780 mg, 35.1%).

MS spectrum [CI/DI (i-Bu)] m/z: 276 (M+1)⁻, 110 (base peak).

IR spectrum (neat) cm$^{-1}$: 2950, 1590, 1310, 1200.

$^1$H-NMR spectrum (CDCl$_3$) δ ppm:

| | |
|---|---|
| 1.5–1.9 | (8H, m), |
| 2.3–2.6 | (2H, m), |
| 2.9–3.0 | (2H, m), |
| 3.20 | (3H, s), |
| 3.41 | (2H, s), |
| 6.73 | (2H, d, J=9Hz), |
| 8.09 | (2H, d, J=9Hz), |

EXAMPLE 19

N-(1-Azabicyclo[3.3.0]octan-5-yl)methyl-N-formyl-2-phenylaniline

The procedures described in Example 2 were repeated except that 2-formylamino-1,1'-biphenyl (286 mg, 1.45 mmol) and 5-chloromethyl-1-azabicyclo[3.3.0]octane (hydrochloride, 300 mg, 1.53 mmol) were employed. In this case, the desired compound was obtained as pale yellow solids (452 mg, 97.3%).

MS spectrum [CI/DI (i-Bu)] m/z: 821 (M+1)⁻, 110 (base peak).

IR spectrum (KBr) cm⁻¹: 3500, 2950, 1680.

¹H-NMR spectrum (CDCl₃) δppm:

| | |
|---|---|
| 1.2–1.3 | (2H, m), |
| 1.6–1.7 | (6H, m), |
| 2.4–2.5 | (2H, m), |
| 2.8–2.9 | (2H, m), |
| 3.0–3.2 | (2H, m), |
| 7.2–7.5 | (9H, m), |
| 8.48 | (1H, s). |

EXAMPLE 20

N-(1-Azabicyclo[3.3.0]octan-5-yl)methyl-N-methyl-2-phenylaniline

The procedures described in Example 3 were repeated except that N-(1-azabicyclo[3.3.0]octan-5-yl)methyl-N-formyl-2-phenylaniline (450 mg, 1.40 mmol) was employed. In this case, the desired compound was obtained as a colorless liquid (383 mg, 89.1%).

MS spectrum [CI/DI (i-Bu)] m/z: 3807 (M+1)⁻, 110 (base peak).

IR spectrum (neat) cm⁻¹: 2950, 1480, 1430, 740.

¹H-NMR spectrum (CDCl₃) δppm:

| | |
|---|---|
| 1.3–1.4 | (2H, m), |
| 1.5–1.8 | (6H, m), |
| 2.4–2.5 | (2H, m), |
| 2.60 | (3H, s), |
| 2.8–2.9 | (2H, m), |
| 2.85 | (2H, s), |
| 7.0–7.1 | (1H, m), |
| 7.2–7.5 | (8H, m). |

EXAMPLE 21

N-(1-Azabicyclo[3.3.0]octan-5-yl)methyl-N-formyl-3-phenylaniline

The procedures described in Example 2 were repeated except that 3-formylamino-1,1'-biphenyl (286 mg, 1.45 mmol) and 5-chloromethyl-1-azabicyclo[3.3.0]octane (hydrochloride, 800 mg, 1.53 mmol) were employed. In this case, the desired compound was obtained as pale yellow solids (385 mg, 82.7%).

MS spectrum [CI/DI (i-Bu)] m/z: 321 (M+1)⁻, 293, 110 (base peak).

IR spectrum (KBr) cm⁻¹: 3500, 2950, 1680.

¹H-NMR spectrum (CDCl₃) δppm:

| | |
|---|---|
| 1.3–1.4 | (2H, m), |
| 1.7–1.8 | (6H, m), |
| 2.4–2.5 | (2H, m), |
| 2.9–3.0 | (2H, m), |
| 3.87 | (2H, s), |
| 7.2–7.6 | (9H, m), |
| 8.43 | (1H, s). |

EXAMPLE 22

N-(1-Azabicyclo[3.3.0]octan-5-yl)methyl-N-methyl-3-phenylaniline

The procedures described in Example 8 were repeated except that N-(1-azabicyclo[3.3.0]octan-5-yl)methyl-N-formyl-3-phenylaniline (370 mg, 1.15 mmol) was employed. In this case, the desired compound was obtained as a colorless liquid (158 mg, 54.8%) The liquid became a solid.

MS spectrum [CI/DI (i-Bu)] m/z: 307 (M+1)⁻, 110 (base peak).

IR spectrum (KBr) cm⁻¹: 2950, 1600, 1490, 760.

¹H-NMR spectrum (CDCl₃) δppm:

| | |
|---|---|
| 1.5–1.6 | (2H, m), |
| 1.7–1.8 | (6H, m), |
| 2.6–2.7 | (2H, m), |
| 3.0–3.1 | (2H, m), |
| 3.11 | (3H, s), |
| 3.33 | (2H, s), |
| 6.8–7.0 | (3H, m), |
| 7.2–7.4 | (5H, m), |
| 7.5–7.6 | (1H, m). |

EXAMPLE 23

N-[2-(1-Azabicyclo[3.3.0]octan-5-yl)ethyl]-2-nitroaniline

The procedures described in Example 12 were repeated except that 1-chloro-2-nitrobenzene (2.04 g, 12.9 mmol) and 5-(2-aminoethyl)-1-azabicyclo[3.3.0]octane (4.00 g, 25.9 mmol) were employed. In this case, the desired compound was obtained as a orange liquid (3.32 g, 98.54%).

MS spectrum (EI/DI) m/z: 275 (M⁻), 154, 110 (base peak).

IR spectrum (neat) cm⁻¹: 8200, 2950, 1600, 1590, 760.

¹H-NMR spectrum (CDCl₃) δppm:

| | |
|---|---|
| 1.6–1.9 | (10H, m), |
| 2.6–2.7 | (2H, m), |
| 3.0–3.1 | (2H, m), |
| 3.3–3.4 | (2H, m), |
| 6.58 | (1H, t, J=8Hz), |
| 6.84 | (1H, d, J=8Hz), |
| 7.40 | (1H, t, J=8Hz), |
| 8.16 | (1H, d, J=8Hz), |
| 9.19 | (1H, brs). |

EXAMPLE 24

N-[2-(1-Azabicyclo[3.3.0]octan-5-yl)-ethyl]-4-nitroaniline

The procedures described in Example 12 were repeated except that 1-chloro-4-nitrobenzene (2 04 g, 12.9 mmol) and 5-(2-aminoethyl)-1-azabicyclo[3.3.0] octane (4.00 g, 25.9 mmol) were employed. In this case, the desired compound was obtained as a yellow liquid (2.93 g, 8 2.5%).

MS spectrum (EI/DI) m/z: 275 (M⁻), 110 (base peak).

IR spectrum (neat) cm⁻¹: 3200, 3000, 1600, 1310.

¹H-NMR spectrum (CDCl₃) δ ppm:

| 1.6–1.8 | (10H, m), |
|---|---|
| 2.6–2.7 | (2H, m), |
| 3.0–3.1 | (2H, m), |
| 3.27 | (2H, t, J=6Hz), |
| 6.44 | (2H, d, J=9Hz), |
| 7.76 | (1H, brs), |
| 8.06 | (2H, d, J=9Hz). |

EXAMPLE 25

N-[2-(1-Azabicyclo[3.3.0]octan-5-yl)ethyl]-N-methyl-2-nitroaniline

The procedures described in Example 12 were repeated except that 1-chloro-2-nitrobenzene (1.87 g, 11.9 mmol) and 5-(2-methylaminoethyl)-1-azabicyclo[3.3.0]octane (4.00 g, 28.8 mmol) were employed. In th is case, the desired compound was obtained as a orange liquid (2.95 g, 85.7%).

MS spectrum (EI/DI) m/z: 289 (M⁻), 154, 110 (base peak).

IR spectrum (neat) cm⁻¹: 2950, 1610, 1510, 1280.

¹H-NMR spectrum (CDCl₃) δppm:

| 1.5–1.6 | (2H, m), |
|---|---|
| 1.6–1.8 | (8H, m), |
| 2.5–2.6 | (2H, m), |
| 2.81 | (3H, s), |
| 2.9–3.0 | (2H, m), |
| 3.1–3.2 | (2H, m), |
| 6.83 | (1H, t, J=8Hz), |
| 7.11 | (1H, d, J=8Hz), |
| 7.38 | (1H, t, J=8Hz), |
| 7.70 | (1H, d, J=8Hz). |

EXAMPLE 26

N-[2-(1-Azabicyclo[3.3.0]octan-5-yl)ethyl]-N-methyl-4-nitroaniline

The procedures described in Example 12 were repeated except that 1-chloro-4-nitrobenzene (1.87 g, 11.9 mmol) and 5-(2-methylaminoethyl)-1-azabicyclo[3.3.0]octane (4.00 g, 23.8 mmol) were employed. In this case, the desired compound was obtained as yellow solids (2.15 g, 62.4%).

MS spectrum (EI/DI) m/z: 289 (M⁻), 165, 110 (base peak).

IR spectrum (KBr) cm⁻¹: 2950, 1590, 1290, 1110.

¹H-NMR spectrum (CDCl₃) δ ppm:

| 1.6–1.9 | (10H, m), |
|---|---|
| 2.6–2.7 | (2H, m), |
| 3.0–3.1 | (2H, m), |
| 3.05 | (3H, s), |
| 3.5–3.6 | (2H, m), |
| 6.63 | (2H, d, J=10Hz), |
| 8.10 | (2H, d, J=10Hz). |

EXAMPLE 27

2-[2-(1-Azabicyclo[3.3.0]octan-5-yl)ethylamino]benzonitrile

2-Fluorobenzonitrile (1.00 g, 8.26 mmol) and 2-(1-azabicyclo[3.3.0]octan-5-yl)ethylamine (3.15 g, 20.4 mmol) were added into anhydrous pyridine (10.0 ml) to react the mixture in a sealed tube for 10.5 hours at 180° C. After addition of water subsequent to concentration in vacuo, the reaction mixture was extracted by ethyl acetate, dried over anhydrous sodium sulfate, concentrated in vacuo, and refined by column chromatography to afford the desired compound (2.02 g, 95.8%), as a colorless liquid.

MS spectrum (EI/DI) m/z: 255 (M⁻), 110 (base peak).

IR spectrum (neat) cm⁻¹: 2955, 2210, 1610, 1520.

¹H-NMR spectrum (CDCl₃) δ ppm:

| 1.6–1.8 | (10H, m), |
|---|---|
| 2.5–2.6 | (2H, m), |
| 3.1–3.2 | (2H, m), |
| 3.33 | (2H, t, J=6Hz), |
| 6.5–6.6 | (2H, m), |
| 7.3–7.4 | (2H, m), |
| 8.00 | (1H, brs). |

EXAMPLE 28

4-[2-(1-Azabicyclo[3.3.0]octan-5-yl)ethylamino]-benzonitrile

The procedures described in Example 1 were repeated except that 4-fluorobenzonitrile (1.00 g, 8.26 mmol ) and 2-(1-azabicyclo[3.3.0]octan-5-yl)ethylamine (3.15 g, 20.4 mmol) were employed. In this case, the desired compound was obtained as a colorless liquid (2.02 g, 99.1%).

MS spectrum (EI/DI) m/z: 255 (M⁻), 110 (base peak).

IR spectrum (neat) cm⁻¹: 2950, 2210, 1610, 1530.

¹H-NMR spectrum (CDCl₃) δ ppm:

| 1.6–1.8 | (10H, m), |
|---|---|
| 2.5–2.6 | (2H, m), |
| 3.0–3.1 | (2H, m), |
| 3.20 | (2H, t, J=6Hz), |
| 6.49 | (2H, d, J=9Hz), |
| 7.13 | (1H, brs), |
| 7.38 | (2H, d, J=9Hz). |

EXAMPLE 29

2-{[2-(1-Azabicyclo[3.3.0]octan-5-yl)ethyl]-methylamino}-benzonitrile

The procedures described in Example 1 were repeated except that 2-fluorobenzonitrile (800 mg, 6.61 mmol) and 5-(2-aminoethyl)-1-azabicyclo[3.3.0]octane (2.78.g, 16.5 mmol) were employed. In this case, the desired compound was obtained as a colorless liquid (2.16 g, quantitative).

MS spectrum [CI/DI (i-Bu)] m/z: 270 [(M+1)⁻, base peak].

IR spectrum (neat) cm⁻¹: 2950, 2210, 1600, 1490.

¹H-NMR spectrum (CDCl₃) δ ppm:

| 1.6–1.8 | (10H, m), |
|---|---|
| 2.5–2.6 | (2H, m), |
| 2.9–3.1 | (2H, m), |
| 2.98 | (3H, s), |
| 3.4–3.5 | (2H, m), |
| 6.81 | (2H, t, J=9Hz), |
| 6.93 | (1H, d, J=9Hz), |
| 7.48 | (1H, t, J=9Hz), |
| 7.50 | (2H, d, J=9Hz). |

EXAMPLE 30

N-[2-(1-Azabicyclo[3.3.0]octan-5-yl)ethyl]-2-chloroaniline

To nitrobenzene (30.0 ml), 2-chloroaniline (600 mg, 4.70 mmol), 5-(2-chloroethyl)-1-azabicyclo[3.3.0]octane (hydrochloride, 1.98 g, 9.42 mmol) and anhydrous potassium carbonate (3.90 g, 28.2 mmol) were added to react same for 10 hours at 120° C. subsequent to addition of 10% aqueous sodium hydroxide solution, the reaction mixture was extracted by ethyl acetate, washed by sodium chloride solution, dried over anhydrous sodium sulfate, concentrated in vacuo, and purified by column chromatography to afford the desired compound (499 mg, 40.1%), as a colorless liquid.

MS spectrum (EI/DI) m/z: 264 (M⁻), 110 (base peak).
IR spectrum (neat) cm⁻¹: 2950, 1600, 1520, 1030.
$^1$H-NMR spectrum (CDCl$_3$) δ ppm:

| | |
|---|---|
| 1.6–1.8 | (10H, m), |
| 2.5–2.6 | (2H, m), |
| 3.0–3.1 | (2H, m), |
| 3.20 | (2H, t, J=6Hz), |
| 6.5–6.6 | (2H, m), |
| 7.10 | (1H, td, J=8, 2Hz), |
| 7.21 | (1H, dd, J=8, 2Hz). |

EXAMPLE 31

N-[2-(1-Azabicyclo[3.3.0]octan-5-yl)ethyl]-2-fluoroaniline

The procedures described in Example 4 were repeated except that 2-fluoroanilins (400 mg, 3.60 mmol) and 5-(2-chloroethyl)-1-azabicyclo[3.3.0]octane (hydrochloride, 1.51 g, 7.20 mmol) were employed. In this case, the desired compound was obtained as a colorless liquid (429 mg, 48.0%).

MS spectrum (EI/DI) m/z: 248 (M⁻), 110 (base peak).
IR spectrum (neat) cm⁻¹: 2950, 1620, 1520, 1190.
$^1$H-NMR spectrum (CDCl$_3$) δppm:

| | |
|---|---|
| 1.6–1.8 | (10H, m), |
| 2.5–2.6 | (2H, m), |
| 3.0–3.1 | (2H, m), |
| 3.18 | (2H, t, J=6Hz), |
| 6.79 | (1H, brs), |
| 6.5–6.7 | (2H, m), |
| 6.9–7.0 | (2H, m). |

EXAMPLE 32

N-[2-(1-Azabicyclo[3.3.0]octan-5-yl)ethyl]-4-fluoro-2-nitroaniline

The procedures described in Example 1 were repeated except that 2,5-difluoronitrobenzene (1.00 g, 6.29 mmol) and 5-(2-aminoethyl)-1-azabicyclo[3.3.0]octane (2.42 g, 15.7 mmol) were employed. In this case, the desired compound was obtained as a colorless liquid (2.00 g, quantitative).

MS spectrum (EI/DI) m/z: 293 (M⁻), 110 (base peak).
IR spectrum (neat) cm⁻¹: 2950, 1520, 1230, 1180.
$^1$H-NMR spectrum (CDCl$_3$) δppm:

| | |
|---|---|
| 1.6–1.8 | (10H, m), |
| 2.6–2.7 | (2H, m), |
| 3.0–3.1 | (2H, m), |
| 3.3–3.6 | (2H, m), |
| 6.82 | (1H, dd, J=9, 5Hz), |
| 7.22 | (1H, ddd, J=9, 4, 3Hz), |
| 7.87 | (1H, dd, J=9, 3Hz), |
| 9.25 | (1H, brs). |

EXAMPLE 33

2-{[2-(1-Azabicyclo[3.3.0]octan-5-yl)ethyl]-amino}benzamide

2-[(1-Azabicyclo[3.3.0]octan-5-yl)ethylamino]benzonitrile (1.34 g, 5.25 mmol) obtained by Example 27 was mixed with concentrated sulfuric acid (48.2 ml) and water 7.5 ml to react the mixture for 2 hours at 110° C. The reaction mixture was cooled to −78° C., neutralized by 25% ammonia solution, extracted by ethyl acetate, washed by water, dried over anhydrous sodium sulfate, concentrated in vacuo, and crystallized from ethyl acetate to afford the desired compound (961 mg, 67.0%).

Melting point: 145°–147° C.
MS spectrum (EI/DI) m/z: 73 (M⁻), 110 (base peak).
IR spectrum (neat) cm⁻¹: 3310, 3150, 1680.
$^1$H-NMR spectrum (CDCl$_3$) δ ppm:

| | |
|---|---|
| 1.6–1.8 | (10H, m), |
| 2.5–2.6 | (2H, m), |
| 3.0–3.1 | (2H, m), |
| 3.20 | (2H, t, J=8Hz), |
| 5.96 | (2H, brs), |
| 6.54 | (1H, t, J=7Hz), |
| 6.70 | (1H, d, J=8Hz), |
| 7.29 | (1H, t, J=7Hz), |
| 7.37 | (1H, d, J=8Hz), |
| 7.80 | (1H, brs). |

EXAMPLE 34

2-[(1-Azabicyclo[3.3.0]octan-5-yl)methylamino]-benzonitrile

The procedures described in Example 1 were repeated except that 2-fluorobenzonitrile (671 mg, 5.54 mmol) and 5-aminomethyl-1-azabicyclo[3.3.0]octane (1.94 g, 13.9 mmol) were employed. In this case, the desired compound was obtained as a colorless liquid (1.26 g, 94.2%).

MS spectrum [CI/DI (i-Bu)] m/z: 242 [(M+1)⁻, base peak].
IR spectrum (neat) cm⁻¹: 2960, 2210, 1610, 1510.
$^1$H-NMR spectrum (CDCl$_3$) δppm:

| | |
|---|---|
| 1.6–1.8 | (10H, m), |
| 2.6–2.7 | (2H, m), |
| 3.0–3.1 | (2H, m), |
| 2.99 | (2H, d, J=5Hz), |
| 5.25 | (1H, brs), |
| 6.6–6.7 | (2H, m), |
| 7.3–7.4 | (2H, m). |

EXAMPLE 35

N-[2-(1-Azabicyclo[3.3.0]octan-5-yl)ethyl]-
2-nitroaniline(hydrochloride)

To N-[2-(1-azabicyclo[3.3.0]octan-5-yl)ethyl]-2-nitroaniline (200 mg, 726 mmol) obtained by Example 23 in ethanol (10 ml), ethanol saturated with hydrogen chloride gas was added dropwise and left to stand to afford the desired salt (217 mg, 95.9%).

Melting point: 219°–223° C.

MS spectrum (EI/DI) m/z: 275 (M⁻), 154, 110 (base peak).

$^1$H-NMR spectrum (DMSO-$d_6$) δppm:

| | |
|---|---|
| 1.8–2.1 | (10H, m), |
| 3.0–3.1 | (2H, m), |
| 3.2–3.3 | (2H, m), |
| 3.4–3.5 | (2H, m), |
| 6.74 | (1H, t, J=8Hz), |
| 7.15 | (1H, d, J=8Hz), |
| 7.55 | (1H, t, J=8Hz), |
| 8.07 | (1H, d, J=8Hz), |
| 8.09 | (1H, brs). |

EXAMPLE 36

N-[2-(1-Azabicyclo[3.3.0]octan-5-yl)ethyl]-
2-nitroaniline(fumarate)

A mixture of N-[2-(1-azabicyclo[3.3.0]octan-5-yl)ethyl]-2-nitroaniline (200 mg, 728 μmol) obtained by Example 23 in ethanol (10 ml) and fumaric acid (84.2 mg, 725 μmol) in ethanol (10 ml) was concentrated until its volume becomes 5 ml and left to stand to afford the desired salt (265 mg, 98.8%).

Melting point: 177°–179° C.

MS spectrum (EI/DI) m/z: 275 (M⁻), 154, 110 (base peak).

$^1$H-NMR spectrum (DMSO-$d_6$) δppm:

| | |
|---|---|
| 1.8–2.1 | (10H, m), |
| 2.7–2.8 | (2H, m), |
| 3.3–3.4 | (2H, m), |
| 3.45 | (2H, t, J=7Hz), |
| 6.50 | (2H, s), |
| 6.68 | (1H, t, J=9Hz), |
| 7.10 | (1H, d, J=9Hz), |
| 7.52 | (1H, t, J=9Hz), |
| 8.05 | (1H, d, J=9Hz). |

EXAMPLE 37

N-[2-(1-Azabicyclo[3.3.0]octan-5-yl)ethyl]-
2-nitroaniline(maleate)

A mixture of N-[2-(1-azabicyclo[3.3.0]octan-5-yl)ethyl]-2-nitroaniline (200 mg, 725 μmol) obtained by Example 23 in ethanol (10 Ml) and maleic acid (84.2 mg, 72 μ mol) in ethanol (10 ml) was concentrated until its volume becomes 3 ml and left to stand to afford the desired salt (223 mg, 78.6%).

Melting point: 94°–95° C.

MS spectrum (EI/DI) m/z: 275 (M⁻), 154, 110 (base peak).

$^1$H-NMR spectrum (DMSO-$dl_6$) δppm:

| | |
|---|---|
| 1.9–2.2 | (10H, m), |
| 3.0–3.2 | (2H, m), |
| 3.2–3.3 | (2H, m), |
| 3.45 | (2H, t, J=7Hz), |
| 6.01 | (2H, s), |
| 6.72 | (1H, t, J=9Hz), |
| 7.12 | (1H, d, J=9Hz), |
| 7.57 | (1H, t, J=9Hz), |
| 8.08 | (1H, d, J=9Hz). |

PHARMACOLOGICAL TEST EXAMPLE (Inhibition against binding of 3H-pirenzepine to brain homogenate of rat)

A brain homogenate of rat was prepared in accordance with the method described by Yamanura and Synder ["Proc. Natr. Acad. Sci. USA", Vol. 71, pages 1725–1729 (1974)]. Namely, SD male rats were killed by decapitation to exentrate each brain. From the brains, each cerebellum was removed and 0.32 M aqueous sucrose solution in 10-folds by volume was added under ice-cooling condition to homogenize the same by a Potter-Elvehjem type glass homogenizer. The resulting homogenate was centrifuged for 10 minutes (1000×g) to obtain a supernatant by removing a precipitate, which supernatant was further homogenized by a homogenizer of "Polytron" to obtain a fraction to be used as a brain homogenate.

Tests were carried out according to the method described by Flynn and Mash ["J. Pharm. Exp. Ther.", Vol. 250, pages 573–581 (1989). Namely, to the brain homogenate (0.035 ml, protein content: 0.6 mg), 550 mM phosphate buffer (pH 7.4, 1 ml) containing 2.0 nM $^3$H-pirenzepine and a Test or Control compound (1 ml, if the test or control compound is solid form, it is dissolved by the 550 mM phosphate buffer) were added to cause a reaction for 60 minutes at room temperature. Then, an ice-cooled buffer (3.0 ml) same with the above was added to the reaction mixture. Thereafter, the mixture was filtrated by a Whattman GF/B filter which was previously dipped in 0.1% polyethyleneimine solution for 60 minutes. The filter was washed twice by the buffer solution (each 3.0 ml) and an emulsion scintillatot for measuring luminescence by a scintillation counter. A 50% inhibition (IC$_{50}$)of the test or control compound against binding of 3H-pirenzepine to brain homogenate was calculated. Results are shown in following Table.

| Compound | | IC$_{50}$ (μM) |
|---|---|---|
| Compounds according to the invention | | |
| Example | 1 | 0.01 |
| | 3 | 0.09 |
| | 6 | 0.03 |
| | 8 | 0.02 |
| | 12 | 0.2 |
| | 13 | 0.3 |
| | 17 | 0.2 |
| | 20 | 0.1 |
| | 23 | 0.1 |
| | 25 | 0.2 |
| | 27 | 0.32 |
| | 28 | 4.57 |
| | 29 | 0.24 |
| | 30 | 0.43 |
| | 31 | 1.59 |
| | 32 | 0.69 |
| | 33 | 1.11 |

| | |
|---|---|
| 34 | 0.55 |
| 36 | 0.09 |
| Controls | |
| THA* | 1.9 |
| 2,8-Dimethyl-3-methylene-1-oxa-8-azabicyclo-[4.5]decane** | 23.6 |
| 1-[N-(1-azabicyclo[3.3.0]octan-5-yl)methyl-N-methylamino]-4-nitronaphthalene*** | 0.04 |
| 1-(1-azabicyclo[3.3.0]octan-5-yl)methylamino-5-nitronaphthalene**** | 0.8 |

In the Table,
*1,2,3,4-tetrahydro-9-aminoacridine,
**compound disclosed in Example 5 of Jap. Pat. No. Hei 2 (A.D. 1990) - 36183(A),
***compound disclosed in Example 15 of Jap. Pat. No. Hei 6 (A.D. 1994) - 184152(A), and
****compound disclosed in Example 17 of Jap. Pat. No. Hei 6 (A.D. 1994) - 184152(A).

What is claimed is:

1. A compound selected from the group consisting of
   (a) N-(1-azabicyclo[3.3.0]octan-5-yl)methyl-N-formylaniline,
   (b) N-(1-azabicyclo[3.3.0]octan-5-yl)methyl-N-methylaniline,
   (c) N-[2-(1-azabicyclo[3.3.0]octan-5-yl)ethyl]-N-formylaniline,
   (d) N-[2-(1-azabicyclo[3.3.0]octan-5-yl)ethyl]-N-methylaniline,
   (e) N-(1-azabicyclo[3.3.0]octan-5-yl)methyl-N-methyl-2-nitroaniline,
   (f) N-(1-azabicyclo[3.3.0]octan-5-yl)methyl-N-methyl-4-nitroaniline,
   (g) N-(1-azabicyclo[3.3.0]octan-5-yl)methyl-N-formyl-2-phenylaniline,
   (h) N-(1-azabicyclo[3.3.0]octan-5-yl)methyl-N-methyl-2-phenylaniline,
   (i) N-(1-azabicyclo[3.3.0]octan-5-yl)methyl-N-formyl-3-phenylaniline,
   (j) N-(1-azabicyclo[3.3.0]octan-5-yl)methyl-N-methyl-3-phenylaniline,
   (k) N-[2-(1-azabicyclo[3.3.0]octan-5-yl)ethyl]-2-nitroaniline,
   (l) N-[2-(1-azabicyclo[3.3.0]octan-5-yl)ethyl]-4-nitroaniline,
   (m) N-[2-(1-azabicyclo[3.3.0]octan-5-yl)ethyl]-N-methyl-2-nitroaniline,
   (n) N-[2-(1-azabicyclo[3.3.0]octan-5-yl)ethyl]-N-methyl-4-nitroaniline,
   (o) 2-[ 2-(1-azabicyclo[3.3.0] octan-5-yl)ethylamino]-benzonitrile,
   (p) 4-[ 2-(1-azabicyclo[3.3.0] octan-5-yl)ethylamino]-benzonitrile,
   (q) 2-{[2-(1-azabicyclo[3.3.0] octan-5-yl)ethyl] methylamino}benzonitrile,
   (r) N-[2-(1-azabicyclo[3.3.0] octan-5-yl)ethyl]-2-chloroaniline,
   (s) N-[2-(1-azabicyclo[3.3.0] octan-5-yl)ethyl]-2-fluoroaniline,
   (t) N-[2-(1-azabicyclo[3.3.0] octan-5-yl)ethyl]-4-fluoronitroaniline,
   (u) 2-{[2-(1-azabicyclo[3.3.0] octan-5-yl)ethyl]amino}-benzamide, and
   (v) 2-[(1-azabicyclo[3.3.0] octan-5-yl)methylamino]-benzonitrile.

2. An agent for improving a cerebral function, which comprises at least one compound selected from the group consisting of
   (a) N-(1-azabicyclo[3.3.0]octan-5-yl)methyl-N-formylaniline,
   (b) N-(1-azabicyclo[3.3.0]octan-5-yl)methyl-N-methylaniline,
   (c) N-[2-(1-azabicyclo[3.3.0]octan-5-yl)ethyl]-N-formylaniline,
   (d) N-[2-(1-azabicyclo[3.3.0]octan-5-yl)ethyl]-N-methylaniline,
   (e) N-(1-azabicyclo[3.3.0]octan-5-yl)methyl-N-methyl-2-nitroaniline,
   (f) N-(1-azabicyclo[3.3.0]octan-5-yl)methyl-N-methyl-4-nitroaniline,
   (g) N-(1-azabicyclo[3.3.0]octan-5-yl)methyl-N-formyl-2-phenylaniline,
   (h) N-(1-azabicyclo[3.3.0]octan-5-yl)methyl-N-methyl-2-phenylaniline,
   (i) N-(1-azabicyclo[3.3.0]octan-5-yl)methyl-N-formyl-3-phenylaniline,
   (j) N-(1-azabicyclo[3.3.0]octan-5-yl)methyl-N-methyl-3-phenylaniline,
   (k) N-[2-(1-azabicyclo[3.3.0]octan-5-yl)ethyl]-2-nitroaniline,
   (l) N-[2-(1-azabicyclo[3.3.0]octan-5-yl)ethyl]-4-nitroaniline,
   (m) N-[2-(1-azabicyclo[3.3.0]octan-5-yl)ethyl]-N-methyl-nitroaniline,
   (n) N-[2-(1-azabicyclo[3.3.0]octan-5-yl)ethyl]-N-methyl-nitroaniline,
   (o) 2-[2-(1-azabicyclo[3.3.0]octan-5-yl)ethylamino]-benzonitrile,
   (p) 4-[2-(1-azabicyclo[3.3.0]octan-5-yl)ethylamino]-benzonitrile,
   (q) 2-{[2-(1-azabicyclo[3.3.0]octan-5-yl)ethyl] methylamino}benzonitrile,
   (r) N-[2-(1-azabicyclo[3.3.0]octan-5-yl)ethyl]-2-chloroaniline,
   (s) N-[2-(1-azabicyclo[3.3.0]octan-5-yl)ethyl]-2-fluoroaniline,
   (t) N-[2-(1-azabicyclo[3.3.0]octan-5-yl)ethyl]-4-fluoro-2-nitroaniline,
   (u) 2-{[2-(1-azabicyclo[3.3.0]octan-5-yl)ethyl]amino}-benzamide, and
   (v) 2-[(1-azabicyclo[3.3.0]octan-5-yl)methylamino]-benzonitrile.

3. An agent as claimed in claim 2, wherein said improvement in cerebral function is attained by actuating muscarine 1 receptor.

4. A method of improving cerebral function, comprising administering to a patient in need of such treatment an effective amount of a compound as claimed in claim 1, in association with a non-toxic pharmaceutical carrier or excipient, to actuate muscarine 1 receptor.

* * * * *